United States Patent [19]

Cornwall et al.

[11] Patent Number: 4,724,851

[45] Date of Patent: Feb. 16, 1988

[54] HAIR FIXATIVE COMPOSITION CONTAINING CATIONIC ORGANIC POLYMER AND POLYDIORGANOSILOXANE

[75] Inventors: Susan M. Cornwall, Owosso; Gretchen S. Kohl, Midland, both of Mich.

[73] Assignee: Dow Corning Corporation, Midland, Mich.

[21] Appl. No.: 926,761

[22] Filed: Nov. 4, 1986

[51] Int. Cl.[4] ............................................. A45D 7/00
[52] U.S. Cl. ...................................................... 132/7
[58] Field of Search ................................ 132/7; 424/70

[56] References Cited

U.S. PATENT DOCUMENTS

| | | | |
|---|---|---|---|
| 3,257,281 | 6/1986 | Maeder | 167/87.1 |
| 4,246,029 | 1/1981 | Sanders, Jr. | 106/8 |
| 4,369,037 | 1/1983 | Matsunaga et al. | 8/127.51 |
| 4,445,521 | 5/1984 | Grollier et al. | 132/7 |
| 4,493,824 | 1/1985 | Abe | 132/7 |
| 4,586,518 | 5/1986 | Cornwall | 132/7 |
| 4,588,760 | 5/1986 | Jachowicz | 132/7 |
| 4,591,610 | 5/1986 | Grollier | 132/7 |

FOREIGN PATENT DOCUMENTS 2114580  2/1983  United Kingdom.

OTHER PUBLICATIONS

"Silicones Provide Real Benefits for Aerosol Cosmetics," by Charles Todd and Steven Hayes, *American Perfumer and Cosmetics*, Oct. 1971.

"Silicones in Hair Care Products," by Michael Starch, *Drug and Cosmetic Industry*, June 1984.

*Primary Examiner*—Gregory E. McNeill
*Attorney, Agent, or Firm*—Marc C. Pawl

[57] ABSTRACT

Hair fixative preparations suitable for application to hair without subsequent rinsing are disclosed containing a mixture of polydiorganosiloxane and a cationic, organic polymer. The preparations are used for setting hair and may be formulated into aerosol mousse, lotion, gel, or cream type products. The preparations are especially effective in providing flexible, long-lasting hold for hair styles.

20 Claims, No Drawings

HAIR FIXATIVE COMPOSITION CONTAINING CATIONIC ORGANIC POLYMER AND POLYDIORGANOSILOXANE

BACKGROUND OF THE INVENTION

This invention relates to a composition for fixing and setting curls in hair. More particularly, the invention relates to the combination of polydiorganosiloxane and cationic organic polymer components in a hair fixative formulation which is applied to hair without subsequent rinsing to provide combable and long-lasting hair styles.

Many popular hair styles require a means to hold the hair in a desired configuration. Several procedures are commonly used for setting hair styles at home and in beauty salons including, for example, the winding of wetted hair around curlers or rods followed by drying; the winding of moist hair around a hot curling iron; and the blow drying of wet hair while rolling the hair around a hand held brush. It is generally recognized that the physical and chemical action of water plays a significant role in the process of setting hair. When hair is wetted, hydrogen bonds in the keratin of hair are broken. Then when hair is shaped using curlers, iron, or brush and dried, hydrogen bonds are reformed at locations different from the previous ones and the hair style is thus set.

When hair is set by the use of water alone, the hair style gradually loses its shape through the absorption of atmospheric moisture and consequent rearrangement of the hydrogen bonds. A considerable number of hair setting compositions have been suggested to improve the durability of hair styles and especially to extend the time period that a set is retained in hair. Such compositions range from the permanent wave types which operate chemically by breaking and reforming disulfide linkages in the hair protein to preparations which provide a thin layer of film forming resin on the hair which tends to bond hair fibers together thereby maintaining a prearranged shape.

Generally, the film forming resin preparations have been composed of water or alcohol solutions of anionic polymers such as polyvinylpyrrolidone, polyvinylpyrrolidonevinylacetate copolymers, polymethacrylate resins, ethyl and butyl monoesters of polymethylvinyl ether and maleic acid, or carboxylated polyvinylacetate copolymers.

Such film forming resins have been used in several different ways. Finishing sprays, for example, are applied as a fine spray (aerosol or pump system) after the hair is styled and dry. Finishing sprays extend the life of a set by providing welds between hair fibers which maintain hold even after moisture has reduced or eliminated hold derived from hydrogen bonds.

In contrast to finishing sprays, presetting preparations are applied to hair prior to shaping and drying. After drying, the hair is manipulated further with the dry resin film already on the hair in order to form the final style. Hold provided by hair fiber welds is ineffective with presetting preparations because the postdrying manipulation generally breaks up the welds. Consequently, a presetting preparation should envelope or impregnate each individual hair fiber with a thin film of resin which, while not binding to other hair fibers, will nevertheless provide the fiber with a longer lasting memory of the imposed set.

When presetting preparations containing conventional resins are used to prolong set memory, they often make the hair objectionably stiff or sticky. In addition the resin tends to produce flaky or linty particles on the hair as the film breaks up during combing or brushing. The sticky and stiff character of the resin films also makes the coated hair difficult to comb or brush and may result in damaging or breaking hairs during such operations.

Organic cationic compounds and polymers such as stearyldimethylbenzylammonium chloride, quaternary nitrogen derivatives of cellulose ethers, and homopolymers and copolymers of dimethyldiallylammonium chloride are well known for use in hair conditioning formulations. Hair conditioners facilitate combing out hair and impart softness and suppleness to the hair. Cationic polymers are further known in the art for their substantivity which enables them to become fixed to hair and to remain on hair. Taking advantage of this substantivity, hair conditioning formulations are generally applied to wet hair which is subsequently rinsed before drying so that more uniform and thinner films of components are left on the hair. In comparison to the anionic polymers, conventional cationics generally show little effect in facilitating the setting of hair styles or providing retention of hair sets over extended periods.

It is a purpose of the present invention to provide improved presetting preparations that facilitate the setting of hair styles; prolong the set memory of hair without making the hair unnaturally stiff or sticky; and provide flexible hold for hair so that it can be combed after setting without substantial loss of set memory.

Todd et al. in "Silicones Provide Real Benefits for Aerosol Cosmetics", *American Perfumer and Cosmetics,* October, 1971, describe the effect of several types of silicones including dimethyl silicones ("dimethicones" by CTFA Cosmetic Ingredient Dictionary nomenclature) used as a modifier for conventional hair fixative resins for hair spray preparations. Maeder in U.S. Pat. No. 3,257,281, June 21, 1966, describes a novel hair fixative resin for use in aerosol hair treatments. The resin contains N,N-dialkylamino substituents which provided water solubility when neutralized with an acid. Maeder further teaches that an antifoam silicone oil is combined with the resin in aerosol hair preparations.

Starch in "Silicones in Hair Care Products", *Drug and Cosmetic Industry,* June 1984, discloses that dimethicone is used in a few commercial conditioners and hair sprays, but because of its tendency to form very hydrophobic films, its use in hair care products is limited. Starch further teaches that silicones which are modified or adapted by substituting some of the methyl groups on silicon by other more hydrophilic groups such as polyoxyalkylene or aminoalkyl groups have a greater variety of applications in hair care products.

Matsunaga et al. in U.S. Pat. No. 4,369,037, Jan. 18, 1983, describe a variety of hair treatment cosmetics containing cationic keratin derivatives. Specifically, a hair conditioner formulation is illustrated which consists of 1 percent cationic keratin and 3 percent dimethyl polysiloxane in water. Matsunaga et al. show that after the conditioner is applied, the hair is rinsed in running water before drying. In contrast, for using cationic keratin in presetting hair fixative formulations, Matsunaga et al. teach a composition which consists of 1 percent cationic keratin, 10 percent ethanol, 0.5 percent of a polyoxyalkylene substituted silicone, 0.1 percent perfume, and the rest water.

Cornwall et al. in U.S. Pat. No. 4,586,518, May 6, 1986, teach a hair setting method in which aminoalkyl substituted polydiorganosiloxane is applied to the hair with or without subsequent rinsing prior to setting. It is further taught that a quaternary nitrogen containing organic conditioner such as a quaternary nitrogen derivative of a cellulose ether may be combined in equal proportions with the aminoalkyl substituted polydiorganosiloxane for use in the hair setting method.

Homan et al. in U.S. patent application Ser. No. 791,047 filed Oct. 24, 1985, which is assigned to the same assignee as the present application, teach hair fixative preparations for leave-on application to hair prior to setting. The preparations contain a blend of cationic organic polymer and carboxyalkyl substituted polydimethylsiloxane. Homan et al. report that these preparations form a flexible film on the hair which holds desired shapes during combing without forming flaky or linty particles. It is further reported that the hold lasts even under humid conditions.

However, none of the above references seem to suggest combining cationic organic resins with unsubstituted polydimethylsiloxanes in a hair fixative formulation for application to hair prior to setting and without subsequent rinsing.

SUMMARY OF THE INVENTION

The present invention relates to a hair fixative composition suitable for application to hair without subsequent rinsing. The composition consists essentially of (A) a polydiorganosiloxane which conforms generally to the formula $QMe_2SiO(MeRSiO)_ySiMe_2Q$ wherein Me denotes the methyl radical; R independently denotes methyl, ethyl, vinyl, or phenyl radicals with the proviso that at least 90 percent of R radicals are methyl, and Q denotes hydroxy, methyl, ethyl, vinyl, or phenyl; and y has an average value from 20 to 2000, and (B) a cationic, organic polymer containing amine or ammonium groups in the polymer chain or joined to the polymer chain, in a suitable aqueous carrier, wherein the weight ratio of (A) to (B) in the composition is within the range of 1:20 to 2:1.

The present invention further relates to a method of setting hair comprising the steps of: moistening the hair with water, applying to the hair an effective amount of the composition of this invention, rolling the hair around a shaping device, and drying the hair while the hair is rolled.

DETAILED DESCRIPTION OF THE INVENTION

The hair fixative compositions of the present invention contain a combination of silicone and cationic organic polymer components. When the composition is applied to hair prior to setting, it forms a film on the hair which prolongs set memory yet leaves the hair feeling and looking naturally soft. Treated hair is also easier to comb when set with the compositions of this invention than when set with the cationic organic polymer only. The composition is especially advantageous in that it produces a flexible film on hair which allows combing the hair without losing the set memory and without forming flaky or linty particles from breakup of the film. Moreover, the film prolongs retention of hair shapes over extended periods of time even under humid conditions.

The cationic, organic polymers used in the present invention are well known materials that typically are nonflowing, solid or rubbery solid materials at room temperature. The polymers are characterized primarily as having amine or ammonium groups either in the polymer chain or in substituents joined to the polymer chain. The amine or ammonium groups provide the polymers with their cationic character which is believed to be responsible for their substantivity to hair. The polymers are generally soluble or readily dispersible in water. The cationic organic polymers are described in detail in UK Patent Application No. 2,114,580 and in U.S. Pat. No. 4,445,521, which are hereby incorporated by reference to further describe and provide examples of the cationic, organic polymers.

Cationic, organic polymers include, among others, quaternary ammonium derivatives of cellulose ethers; copolymers of hydroxyethylcellulose and dimethyldiallylammonium halide; copolymers of vinylpyrrolidone and dimethylaminoethylmethacrylate; terpolymers of vinylcaprolactam, vinylpyrrolidone, and dimethylaminoethylmethacrylate; quaternary ammonium derivatives of copolymers of vinylpyrrolidone and dimethylaminoethylmethacrylate; copolymers of acrylamide and dimethyldiallylammonium halide; and quaternary ammonium derivatives of copolymers of acrylamide and dimethylaminoethylmethacrylate. Although any of the cationic, organic polymers can be used in the compositions of this invention, polymers containing quaternary ammonium groups are preferred. Compositions containing these polymers provide more effective and more durable films when applied to hair.

Specific preferred polymers include quaternary ammonium derivatives of cellulose ethers, copolymers of hydroxyethylcellulose and dimethyldiallylammonium halide, quaternary ammonium derivatives of copolymers of vinylpyrrolidone and dimethylaminoethylmethacrylate, copolymers of acrylamide and dimethyldiallylammonium halide, and quaternary ammonium derivatives of copolymers of acrylamide and dimethylaminoethylmethacrylate. Among the preferred polymers, the copolymers of acrylamide and dimethyldiallylammonium halide and the copolymers of hydroxyethylcellulose and dimethyldiallylammonium halide are most preferred.

The polydiorganosiloxanes used in the present invention range from thin fluids having a viscosity of about 20 cs at 25° C. to thick gums having viscosities of a million centistokes or more. The diorganosiloxane polymers are generally described by the formula

wherein Me denotes the methyl radical; each R independently denotes methyl, ethyl, vinyl, or phenyl radicals, and Q denotes hydroxy, methyl, ethyl, vinyl, or phenyl radicals. The diorganosiloxane polymers most useful in this invention are predominately methyl substituted polymers wherein at least 90 percent of R radicals in the formula are methyl groups. It is most preferred to use polydimethylsiloxanes wherein essentially all R radicals are methyl groups. However, minor amounts, up to about 10 percent, of other hydrophobic substituents such as ethyl, vinyl, and phenyl generally do not change the character of polydimethylsiloxanes greatly and such polymers are anticipated to function equivalently in the present invention. The polymer chains may be terminated by triorganosiloxane units such as trimethylsiloxane and dimethylvinylsiloxane or by hydroxyl groups.

In the general formula for polydiorganosiloxanes, the value of y is referred to as the degree of polymerization of the polymer. This value essentially determines the viscosity of the polymer and may vary from about 20 to 2000 for the materials most useful in this invention. Generally, polydiorganosiloxane having a viscosity of about 200 to 15,000 cs at 25° C. are preferred because they can be more easily emulsified in water and because they perform advantageously with a wide range of cationic, organic resins. Polydiorganosiloxane within the preferred range of viscosities have average degrees of polymerization of from about 100 to about 600.

The polydimethylsiloxanes are known materials (referred to as "dimethicone" in the CTFA Cosmetic Ingredient Dictionary) which are commercially available in a variety of viscosities. Polydimethylsiloxanes are hydrophobic oils which are insoluble in water. Consequently, in order to form fixative preparations suitable for application to hair, they are dispersed in water with the aid of one or more surfactants to form stable emulsions. Emulsions of polydimethylsiloxanes are typically cloudy or milky white in appearance and have discrete domains or particles of silicone (ranging in size from about 120 nm to 1000 nm) dispersed uniformly throughout the water carrier.

Emulsions of polydimethylsiloxanes are also well known and commercially available. They can be prepared by mixing the silicone in water with one or more surfactants. Any surfactant selected from the group consisting of cationic surfactants, anionic surfactants, and nonionic surfactants can be used to help stabilize the emulsion according to well known processes. Often it is advantageous for improved stability, to use a mixture of two or more surfactants such as a mixture of two nonionic surfactants, a mixture of an anionic and a nonionic surfactant, or a mixture of a cationic and a nonionic surfactant. Generally, from about 1 to 30 parts by weight of surfactants are used in the emulsion for each 100 parts by weight of silicone. Emulsification methods of polydimethylsiloxanes are described further in U.S. Pat. No. 4,246,029, which is hereby incorporated by reference.

Hair fixative compositions are prepared by forming an aqueous dispersion or emulsion of the silicone in an aqueous solution of the organic polymer. The silicone may be emulsified into an aqueous medium which already contains the organic polymer or the silicone may be first emulsified in water and then the silicone emulsion combined with a second solution containing the organic polymer. Alternatively, the organic polymer may be dissolved in a preformed emulsion of the silicone.

The combination of cationic, organic polymer and polydiorganosiloxane is diluted in the aqueous carrier liquid to facilitate obtaining even and effective treatment of the hair. The carrier liquid can be water only or it can be a mixture of water and a compatible organic solvent including alcohols such as ethanol and isopropanol and glycols such as propylene glycol or other solvents as well known in the hair care art.

The amount of carrier used in the compositions is not critical and can vary over a wide range. Usually, it is preferred, for ease of application, to use compositions containing from 0.1 to about 20 percent by weight of the combination of silicone and organic polymer. It is even more preferred that the composition contain 0.5 to 8 percent by weight of the combination of silicone and organic polymer.

The weight ratio of silicone to organic polymer in the compositions of the present invention is within the range of about 1:20 to 2:1 inclusive. For example, the composition may contain 10 parts silicone and 90 parts organic polymer, 50 parts silicone and 50 parts organic polymer, or 65 parts silicone and 35 parts organic polymer. It is even more preferred to use compositions wherein the proportion of silicone to organic polymer is in the range of 1:10 to 1:1 inclusive. Compositions with the above ratio of components are preferred because they generally provide a very desirable combination of flexible fixation and conditioning effects on hair.

The compositions of this invention provide many improvements in hair characteristics that are not obtained by the use of either silicone or organic polymer alone. For example, on wet hair, the composition improves the ease of wet combing and provides a silkier touch. Once the treatment is dried, a film is formed on individual hair strands which mechanically holds the shape of the hair, but the hair continues to exhibit silkier touch and easy combing characteristics. While the organic polymer alone may provide some silkiness and improved combing, the combination with polydiorganosiloxane enhances these properties. Typically, the organic polymer alone has a tacky feel which is detackified upon addition of the silicone. Similarly, while the organic polymer alone on hair may provide some set memory effect, the combination of silicone and organic polymer on hair provides better set memory because the set is more durable, longer lasting, flexible, and lubricated for improved combing ease. The compositions of this invention containing unmodified silicones also have the added advantage that the silicone is not substantive to hair and consequently will not build up on the hair even with frequent use.

The compositions of this invention may also contain other components such as thickeners, perfumes, colorants, propellant gases and small amounts of acids or bases to adjust pH as desired. When the composition is intended to be applied to the hair by first placing a portion in the hand and then transferring to the hair, it is preferred that the composition contain a thickener. The concentration of thickeners when used is generally from 0.5 to 30 percent, and preferably from 0.5 to 15 percent by weight.

Thickeners which can be used include sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose and starch amylose and locust bean gum.

Perfumes which can be used in the compositions are the cosmetically acceptable perfumes and they may be present in amounts which vary from 0.1 to 0.5 percent by weight.

When the composition is intended for aerosol preparations such as mousses, propellant gases can be included such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane.

The present invention further relates to a method of setting hair comprising the steps of: moistening the hair with water, applying to the hair an effective amount of the composition of this invention, rolling the hair around a shaping device, and drying the hair while the hair is rolled. The steps of the method of this invention may be performed in any order or simultaneously with the only exception being that the hair is dried while the hair is rolled and, of course, after the hair has been moistened with water and treated with the fixative composition of this invention.

In the method of this invention, a desired shape or configuration is imposed on the hair by rolling the hair around a shaping device. Any of the conventional devices commonly used for setting hair styles may be employed in the method of this invention. For example the hair may be rolled on curlers, a curling iron or a hand held brush. The hair may be rolled while wet such as after shampooing or it may be rolled while dry and then moistened with water. Moistening of dry rolled hair may also be accomplished simultaneously with the application of the treatment composition since the hair fixative composition is delivered in an aqueous emulsion.

In the method of this invention, the composition may be applied to the surface of the hair in any suitable manner such as by massaging the composition throughout the hair by hand, by dipping the hair into the composition, by brushing or combing the composition through the hair, or by padding the hair with sponges or cloth containing absorbed treating composition. The composition may be applied either before the hair is rolled or after it is rolled. Generally, however, it is preferred to apply the composition prior to rolling the hair since it is easier to treat the hair evenly at this stage.

The hair fixative composition is formulated so that it is suitable to be applied to the hair without subsequent water rinsing. Such leave-on compositions of this invention are preferred because they provide longer-lasting shape holding properties to hair.

Generally the amount of composition is applied that is effective to provide an improvement in curl retention. The amount required will vary with the quantity and type of hair of each individual. Also the amount applied will vary depending on the extent of curl retention desired. Appropriate amounts for any individual's hair are readily determined by one or two trial applications.

The hair is dried while it is rolled in the desired shape or configuration. The hair may be dried by any convenient method such as by heating the hair with a blow dryer, with hot curlers, or with a heated curling iron. The hair may also be allowed to dry naturally at room temperature.

The following examples are presented to illustrate the invention to those skilled in the art and should not be construed as limiting the invention, which is properly delineated in the appended claims. All proportions by parts or percents are by weight unless otherwise stated.

EXAMPLE 1

This example compares the curl durability of hair which has been set after a treatment with either the cationic organic polymer or polydiorganosiloxane by itself or with a mixture of cationic organic polymer and polydiorganosiloxane.

Dark brown European hair tresses were prepared in two gram bundles with a length of five inches. Hair tresses were treated by massaging 0.5 cc of the hair fixative composition into the hair for 30 seconds and then combing three times. Next, each tress was individually rolled onto a ¾ inch O.D. curler and allowed to dry 12 to 14 hours at low humidity (<30% RH). Tresses were removed from the curlers, and hung in front of a calibrated board in a room at 70% RH, and then combed three times. The tress lengths were measured both prior to and immediately after combing and again 2, 4, 8, and 24 hours later. Curl drops were calculated by subtracting the length prior to combing from the subsequent lengths. The tresses were also evaluated (on a scale of 1 to 5 with lower numbers indicating preferred characteristics) for dry feel and dry comb.

Hair tresses were treated with aqueous mixtures of a cationic organic copolymer and either trimethylsiloxane terminated polydimethylsiloxane (PDMS) or, for comparison, a modified polydimethylsiloxane containing polyoxyalkylene substituents (PDMS-POA). The cationic organic polymer used in the hair fixative compositions was a copolymer of hydroxyethylcellulose and dimethyldiallylammonium chloride which is commercially available as CELQUAT L200 from National Starch & Chemical Corporation, Bridgewater, N.J.

An aqueous emulsion of silicone was used which contained about 60% of PDMS having a viscosity of about 350 cs at 25° C., 3.5% of polyoxyethylene (6) isolauryl ether (a nonionic surfactant for stabilizing the silicone emulsion), and 0.23% of tallow trimethyl ammonium chloride (a cationic surfactant for stabilizing the silicone emulsion), 0.25% of propylene glycol, and 0.15% of preservatives. The silicone emulsion was milky, white in appearance and had an average particle diameter of 300 nm.

In comparison mixtures, a polyoxyalkylene substituted silicone was used which had a viscosity of 1,000 cs at 25° C., was compatible with water, and was a polymer averaging 157 dimethylsiloxane units and 21 methylpolyoxyalkylenesiloxane units per molecule with about 60 mole % of the polyoxyalkylene substituents being about 36 units long with an equal mix of oxyethylene and oxypropylene units and with the remaining polyoxyalkylene substituents being about 12 units long with all oxyethylene units.

Hair fixative compositions were prepared by mixing the above components in various proportions as shown in Table 1. The curl drops observed with two duplicate tresses for each treatment are also shown in Table 1.

In Table 1, a shorter curl drop indicates improved set memory in comparison to a longer curl drop. The data shows that polydimethylsiloxane alone does not improve set memory. However, with a mixture of cationic organic polymer and polydimethylsiloxane the set memory is improved greatly. The data also illustrates that mixtures of organic polymer and polydimethylsiloxane surprisingly give better set memory than mixtures of organic polymer and polyoxyalkylene substituted silicone. It was also observed that dry hair released more easily from the curlers after treatments with mixtures of silicone and organic resin than when treated with only the organic resin.

TABLE 1

| Hair Fixative Composition (percent by weight) | | | Curl Drop (cm) | | | | |
|---|---|---|---|---|---|---|---|
| CELQUAT | PDMS | PDMS-POA | 0 hr | 2 hr | 4 hr | 8 hr | 24 hr |
| 3 | 0 | 0 | 0.7 | 0.9 | 0.9 | 1.4 | 1.5 |
|   |   |   | 0.7 | 0.9 | 1.5 | 1.5 | 1.5 |
| 1.5 | 0 | 0 | 0.7 | 0.9 | 0.9 | 1.0 | 1.3 |
|   |   |   | 0.7 | 0.9 | 1.0 | 1.3 | 2.5 |
| 1.5 | 1.5 | 0 | 0.7 | 1.0 | 1.1 | 1.6 | 2.1 |
|   |   |   | 0.4 | 0.6 | 0.7 | 0.7 | 0.9 |

TABLE 1-continued

| Hair Fixative Composition (percent by weight) | | | Curl Drop (cm) | | | | |
|---|---|---|---|---|---|---|---|
| CELQUAT | PDMS | PDMS-POA | 0 hr | 2 hr | 4 hr | 8 hr | 24 hr |
| 2.1 | 0.9 | 0 | 0.4 | 0.5 | 0.7 | 0.8 | 1.6 |
|  |  |  | 0.7 | 0.7 | 0.9 | 1.3 | 1.9 |
| 2.7 | 0.3 | 0 | 0.7 | 0.7 | 0.9 | 1.2 | 1.4 |
|  |  |  | 0.7 | 0.7 | 0.9 | 1.1 | 1.3 |
| 1.5 | 0 | 1.5 | 1.0 | 1.1 | 1.6 | 2.0 | 2.9 |
|  |  |  | 0.6 | 0.8 | 1.2 | 1.5 | 2.0 |
| 2.1 | 0 | 0.9 | 0.9 | 1.3 | 1.7 | 2.0 | 6.0 |
|  |  |  | 0.7 | 1.0 | 1.1 | 1.4 | 1.8 |
| 2.7 | 0 | 0.3 | 0.6 | 0.6 | 0.7 | 0.7 | 4.0 |
|  |  |  | 0.9 | 1.4 | 1.4 | 1.4 | 1.6 |
| 0 | 1.5 | 0 | 1.6 | 1.8 | 2.5 | 3.3 | 5.3 |
|  |  |  | 1.5 | 2.2 | 2.6 | 3.5 | 6.0 |
| 0 | 0 | 1.5 | 2.0 | 3.0 | 4.5 | 5.5 | 7.5 |
|  |  |  | 1.5 | 2.2 | 2.5 | 3.2 | 4.5 |
| Control (water only) | | | 2.6 | 3.6 | 4.0 | 4.6 | 6.6 |
|  |  |  | 1.4 | 1.7 | 2.2 | 2.7 | 5.7 |

After the curl drop evaluation, several of the tresses were moistened and again rolled on curlers without additional treatment. After drying, the tresses were unrolled and evaluated by a panel of five judges for ease of combing and feel. The tresses were evaluated on a scale of 1 to 5 where 1 indicates the most desirable characteristic and 5 the least desirable. Averages of the five evaluations are shown in Table 2.

TABLE 2

| Hair Fixative Composition (percent by weight) | | | Average of Evaluation | |
|---|---|---|---|---|
| CELQUAT | PDMS | PDMS-POA | Combing | Feel |
| 3 | 0 | 0 | 4.1 | 2.9 |
| 1.5 | 0 | 0 | 3.1 | 2.5 |
| 1.5 | 1.5 | 0 | 2.5 | 2.4 |
| 1.5 | 0 | 1.5 | 3.0 | 2.4 |
| 0 | 1.5 | 0 | 1.9 | 1.9 |
| Control (water only) | | | 2.9 | 1.7 |

The data in Table 2 show that fixative compositions of this invention improve combing and feel aesthetics of the hair as well as providing optimum set memory enhancement.

EXAMPLE 2

A hair fixative composition was prepared containing 2.5% of CELQUAT L200 and 2.5% polydiorganosiloxane by dissolving the organic resin in water and adding an appropriate portion of the silicone emulsion described in Example 1. Five tresses were treated with the composition and tested for curl retention according to the procedure of Example 1. For comparison, control tests were made using only water or only a 5% CELQUAT solution as the treatment. The average curl drop for the treatments is shown in Table 3.

TABLE 3

|  | Curl Drop (cm) | | | |
|---|---|---|---|---|
| Hair Fixative Composition | 2 hr | 4 hr | 8 hr | 24 hr |
| water | 1.7 | 2.6 | 3.6 | 5.6 |
| CELQUAT only | 0.4 | 0.7 | 1.0 | 2.2 |
| CELQUAT-PDMS | 0.4 | 0.7 | 1.1 | 1.5 |

EXAMPLE 3

This example illustrates the use of several different polydimethylsiloxanes and emulsion forms in aqueous mixtures with a copolymer of acrylamide and dimethyldiallylammonium chloride.

Composition I was prepared by mixing 0.42 g of the silicone emulsion described in Example 1 with 3.13 g of MERQUAT S (an 8% solids aqueous solution of a resinous copolymer of acrylamide and dimethyldiallylammonium chloride available form Merck & Company, Inc, Rahway, N.J.) and 6.45 g of water.

Composition II was prepared by mixing 0.71 g of a silicone gum emulsion with 3.13 g of MERQUAT S and 6.16 g of water. The silicone gum emulsion contained 35% polydimethylsiloxane having a viscosity at 25° C. of 100,000 cs. The gum emulsion was prepared by emulsion polymerization of dimethylsiloxane cyclics and was stabilized with 2.3% of polyoxyethylene (10) nonylphenyl ether, a nonionic surfactant, and 1.9% of dodecylbenzene sulfonic acid neutralized with triethanol amine, an anionic surfactant. The emulsion was milky white and had an average particle diameter of 180 nm.

Composition III was prepared by mixing 0.42 g of an anionic silicone emulsion with 3.13 g of MERQUAT S and 6.45 g of water. The anionic silicone emulsion contained 60% polydimethylsiloxane having a viscosity at 25° C. of 350 cs. The emulsion was stabilized with 3.8% of polyoxyethylene (6) isolauryl ether a nonionic surfactant and 0.23% of sodium alkylaryl polyether sulfate, an anionic surfactant commercially available as TRITON W-30, Rohm and Haas Company, Inc., Philadelphia, PA. The anionic silicone emulsion was milky white and had an average particle diameter of 270 nm.

Compositions I, II, and III each contained 2.5% of polydimethylsiloxane and 2.5% of organic resin. Five tresses were treated with each composition and tested for curl retention according to the procedure of Example 1. For comparison, control tests were made using only water or only a 5% organic resin solution as the treatment. The average curl drop for the treatments is shown in Table 4.

TABLE 4

|  | Curl Drop (cm) | | | |
|---|---|---|---|---|
| Hair Fixative Composition | 2 hr | 4 hr | 8 hr | 24 hr |
| water | 1.7 | 2.6 | 3.6 | 5.6 |
| MERQUAT S only | 1.2 | 1.7 | 2.6 | 4.1 |
| I | 1.6 | 1.9 | 2.2 | 2.9 |
| II | 1.6 | 2.3 | 3.1 | 4.8 |
| III | 1.6 | 3.3 | 4.2 | 5.7 |

The data in Table 4, indicates that with this particular organic resin, a cationic emulsion of silicone provides a longer lasting enhancement of set memory.

That which is claimed is:

1. A hair fixative composition suitable for application to hair without subsequent rinsing which composition consists essentially of
   (A) a polydiorganosiloxane which conforms generally to the formula QMe$_2$SiO(MeRSiO)$_y$SiMe$_2$Q wherein Me denotes the methyl radical; R independently denotes methyl, ethyl, vinyl, or phenyl radicals with the proviso that at least 90 percent of R radicals are methyl, and Q denotes hydroxy, methyl, ethyl, vinyl, or phenyl; and y has an average value from 20 to 2000, and
   (B) a cationic, organic polymer containing amine or ammonium groups in the polymer chain or joined to the polymer chain, in a suitable aqueous carrier, wherein the weight ratio of (A) to (B) in the composition is within the range of 1:20 to 2:1.

2. The composition of claim 1 wherein the cationic, organic polymer is selected from the group consisting of quaternary ammonium derivatives of cellulose ethers; copolymers of hydroxyethylcellulose and dimethyldiallylammonium halide; copolymers of vinylpyrrolidone and dimethylaminoethylmethacrylate; terpolymers of vinylcaprolactam, vinylpyrrolidone, and dimethylaminoethylmethacrylate; quaternary ammonium derivatives of copolymers of vinylpyrrolidone and dimethylaminoethylmethacrylate; copolymers of acrylamide and dimethyldiallylammonium halide; and quaternary ammonium derivatives of copolymers of acrylamide and dimethylaminoethylmethacrylate.

3. The composition of claim 1 wherein the cationic, organic polymer contains quaternary ammonium groups.

4. The composition of claim 3 wherein the cationic, organic polymer is selected from the group consisting of quaternary ammonium derivatives of cellulose ethers, copolymers of hydroxyethylcellulose and dimethyldiallylammonium halide, quaternary ammonium derivatives of copolymers of vinylpyrrolidone and dimethylaminoethylmethacrylate, copolymers of acrylamide and dimethyldiallylammonium halide, and quaternary ammonium derivatives of copolymers of acrylamide and dimethylaminoethylmethacrylate.

5. The composition of claim 4 wherein the polydiorganosiloxane is trimethylsiloxane terminated polydimethylsiloxane.

6. The composition of claim 5 wherein y has an average value of 100 to 600.

7. The composition of claim 6 wherein the ratio of (A) to (B) in the composition is within the range of 1:10 to 1:1.

8. The composition of claim 7 wherein the composition contains 0.1 to 20 percent by weight of the combination of (A) and (B).

9. The composition of claim 8 wherein the carrier comprises water and the polydiorganosiloxane is dispersed in the water with a surfactant selected from the group consisting of anionic, cationic, and nonionic surfactants.

10. The composition of claim 9 wherein the composition contains 0.5 to 8 percent by weight of the combination of (A) and (B).

11. A method of setting hair comprising the steps of: moistening the hair with water, applying to the hair an effective amount of a composition consisting essentially of (A) a polydiorganosiloxane which conforms generally to the formula

wherein Me denotes the methyl radical; R independently denotes methyl, ethyl, vinyl, or phenyl radicals with the proviso that at least 90 percent of R radicals are methyl, and Q denotes hydroxy, methyl, ethyl, vinyl, or phenyl; and y has an average value from 20 to 2000, and (B) a cationic, organic polymer containing amine or ammonium groups in the polymer chain or joined to the polymer chain, in a suitable aqueous carrier, wherein the weight ratio of (A) to (B) in the composition is within the range of 1:20 to 2:1, rolling the hair around a shaping device, and drying the hair while the hair is rolled.

12. The method of claim 11 wherein the cationic, organic polymer is selected from the group consisting of quaternary ammonium derivatives of cellulose ethers; copolymers of vinylpyrrolidone and dimethylaminoethylmethacrylate; terpolymers of vinylcaprolactam, vinylpyrrolidone, and dimethylaminoethylmethacrylate; quaternary ammonium derivatives of copolymers of vinylpyrrolidone and dimethylaminoethylmethacrylate; copolymers of acrylamide and dimethyldiallylammonium halide; and quaternary ammonium derivatives of copolymers of acrylamide and dimethylaminoethylmethacrylate.

13. The method of claim 11 wherein the cationic, organic polymer contains quaternary ammonium groups.

14. The method of claim 13 wherein the cationic, organic polymer is selected from the group consisting of quaternary ammonium derivatives of cellulose ethers, quaternary ammonium derivatives of copolymers of vinylpyrrolidone and dimethylaminoethylmethacrylate, copolymers of acrylamide and dimethyldiallylammonium halide, and quaternary ammonium derivatives of copolymers of acrylamide and dimethylaminoethylmethacrylate.

15. The method of claim 14 wherein the polydiorganosiloxane is trimethylsiloxane terminated polydimethylsiloxane.

16. The method of claim 15 wherein y has an average value of 100 to 600.

17. The method of claim 16 wherein the ratio of (A) to (B) in the composition is within the range of 1:10 to 1:1.

18. The method of claim 17 wherein the composition contains 0.1 to 20 percent by weight of the combination of (A) and (B).

19. The method of claim 18 wherein the carrier comprises water and the polydiorganosiloxane is dispersed in the water with a surfactant selected from the group consisting of anionic, cationic, and nonionic surfactants.

20. The method of claim 19 wherein the composition contains 0.5 to 8 percent by weight of the combination of (A) and (B).

* * * * *